United States Patent [19]

Suciu

[11] 4,304,917
[45] Dec. 8, 1981

[54] CRYSTALLIZATION PROCESS

[75] Inventor: George D. Suciu, Ridgewood, N.J.

[73] Assignee: The Lummus Company, Bloomfield, N.J.

[21] Appl. No.: 160,684

[22] Filed: Jun. 18, 1980

Related U.S. Application Data

[63] Continuation of Ser. No. 30,091, Apr. 16, 1979, abandoned.

[51] Int. Cl.³ .................. C07D 239/02; C07D 213/56
[52] U.S. Cl. ...................................... 546/317; 260/707
[58] Field of Search ....... 546/317; 260/707, DIG. 35; 23/295 R; 422/254; 210/738, 774; 62/544, 545

[56] References Cited

U.S. PATENT DOCUMENTS

| | | | |
|---|---|---|---|
| 2,743,197 | 4/1956 | Hastings | 422/254 |
| 2,833,835 | 5/1958 | Green | 422/254 |
| 4,008,241 | 2/1977 | Gelbein | 546/317 |

OTHER PUBLICATIONS

Crystallization: Theory and Practice, Van Hook Reinhold Publishing Corp., N.Y., 1961, pp. 212-216.

*Primary Examiner*—Ernest G. Therkorn
*Attorney, Agent, or Firm*—Louis E. Marn; Elliot M. Olstein

[57] ABSTRACT

In the crystallization of a material from a liquid solution thereof wherein normal rapid cooling produces a non-filterable solid, the mixture of material and liquid is subjected to a high shear force field to produce a filterable slurry of the material, with the mixture being subjected to the shear force either during the cooling or subsequent thereto. The process is particularly applicable to recovering nicotinamide from a supersaturated aqueous solution thereof.

6 Claims, No Drawings

CRYSTALLIZATION PROCESS

This is a continuation of application Ser. No. 030,091, filed Apr. 16, 1979, now abandoned.

This invention relates to recovery of solids from a solution of crystallization. This invention is particularly applicable to crystallization of nicotinamide from an aqueous solution thereof.

In many processes wherein a material is to be recovered from a solution by cooling the solution to a temperature below the incipient crystallization temperature; in particular, from a supersaturated solution, undesired spontaneous nucleation in the bulk of the solution occurs, resulting in the formation of a solid mass which cannot be stirred, pumped, filtered, or washed conveniently. Thus, for example, in the production of nicotinamide, such nicotinamide is recovered as a water solution, with the hot solution being subsequently cooled to crystallize the nicotinamide to thereby separate the nicotinamide from water soluble impurities, such as nicotinic acid. Nicotinamide is characterized by a very high solubility in water (completely miscible above 55° C.) and a tendency to form supersaturated solutions. At high supersaturation levels, undesired spontaneous nucleation occurs, and at the concentration levels generally encountered; e.g., sixty to seventy percent nicotinamide, the resulting crystals adhere to each other and transform the content of the crystallizer into a solid mass which cannot be stirred, pumped, filtered, or washed conveniently. In order to maintain the flow properties of the slurry, one of the current practices is to perform the cooling in stages. During the first stage, the hot solution is cooled at a convenient rate until the temperature of incipient crystallization (40° to 45° C.), and from this point on the cooling proceeds (second stage) at a strictly controlled rate of 1° C. per hour until the majority of the amide has crystallized (32° C.). During the third state, the temperature is lowered as rapidly as possible to the filtration temperature (10° to 15° C.). The slow cooling during the second stage is required in order to obtain a filterable slurry, and depending on the concentration of the initial solution, the cooling process may take six to eight hours.

In accordance with another procedure, the nicotinamide is recrystallized from a convenient organic solvent in which the solubility is lower than water; however, such a procedure requires the additional step of removing organic solvent adhering to the crystals and effecting recovery thereof.

In accordance with the present invention, a material is recovered from a liquid solution thereof by cooling the solution to recover the material by crystallization of the material from the solution, with the mixture of material and liquid being subjected to a high shear force (during the cooling or subsequent thereto) to produce a filterable slurry of the material in the liquid. Applicant has found that a filterable slurry of the material in the liquid can be produced from a solution which when subjected to rapid crystallization cooling would normally produce a non-filterable solid-like mixture of material and liquid, provided that the mixture of material and liquid is subjected to a high shear force during the cooling or after formation of the solid-like mixture of material and liquid. Thus, in accordance with the present invention, the solution may be rapidly cooled while subjecting the solution to a shear force sufficient to produce a filterable slurry. Alternatively, the solution may be rapidly cooled (without application of such shear force) and the formed solid-like aggregate or mixture is subjected to a shear force sufficient to convert the solid aggregate or mixture to a filterable slurry.

The high shear force may be applied to the solid by use of any one of a wide variety of apparatus capable of providing a shear force field. Thus, for example, the equipment may be one-or two-screw grinders, Z-blade mixers, vibrating mixers and the like. The shear force which is applied will vary with the concentration of the solution (in general higher forces are required at higher concentrations), the particular type of solid, and other characteristics. As should be apparent, the power input, velocity or frequency and amplitude of the active shearing elements are controlled to provide a shear force which is sufficient to produce a filterable slurry of the material. The selection of the particular shear force required to produce a filterable slurry is deemed to be well within the scope of those skilled in the art from the teachings herein, and as a result, no further details in this respect are deemed necessary for a complete understanding of the present invention.

Although the invention is of general applicability to recovery of a material from a solution wherein rapid cooling of the solution to produce solidification would normally produce a non-filterable solid, the present invention has particular applicability to the recovery of nicotinamide from aqueous solutions thereof, such as those resulting in the production of nicotinamide from nicotinonitrile. In general, such solutions have a nicotonamide concentration of at least 40%, most generally at least 50% and most generally the nicotinamide concentration does not exceed 85%. The aqueous solution also generally contains as an impurity nicotinic acid, generally present as a mmonium nicotinate. Such an aqueous solution may be produced, for example, by the procedure disclosed in U.S. Pat. No. 4,008,241, although as should be apparent the present invention is not limited to aqueous solutions of nicotinamide produced by such a procedure.

In accordance with the present invention, such an aqueous solution of nicotinamide is cooled to solidify the nicotinamide from the aqueous solution, without slow cooling; i.e., cooling is effected at the maximum practicable cooling rate, with the mixture being subjected to a shear force field sufficient to produce a filterable slurry either during or subsequent to such cooling. In this manner, nicotinamide may be recovered and separated from a mother liquor which contains the nicotinic acid impurity. The recovered nicotinamide crystals may then be washed to remove nicotinic acid dissolved in the mother liquor which adheres to the crystals after filtration.

The recovery of a compound from a solution in accordance with the present invention may be effected in a batch or continuous manner. The invention offers the advantage that filterable slurries are obtained irrespective of cooling rate whereby cooling can be conducted at the maximum practicable rate to reduce the overall time for solid recovery. In addition, strict control procedures over lengthy periods of time are no longer required.

The invention will be further described with respect to the following examples; however, the scope of the invention is not to be limited thereby:

EXAMPLE 1

500 g of a hot mixture containing 65% nicotinamide, 5% nicotinic acid (as ammonium nicotinate) and the rest water is cooled in a beaker placed in an ice-water bath. The first crystals appear at 42° C. at 30° C. the mixture cannot be stirred any more. When a thermocouple implanted in various points of the solid mass which has formed shows 10°–15° C., the mass is cut to conveniently-sized pieces and fed to a worm grinder, which was previously cooled. A thick paste results, from which upon filtration, 70 g filtrate are obtained.

The possibility of purifying the nicotinamide crystals from the nicotinic acid existing in the initial solution, by using the procedure of the present disclosure, is proven in Example 2.

EXAMPLE 2

A hot mixture containing 65% nicotinamide, 5% nicotinic acid (as ammonium nicotinate) and the rest water is cooled in an ice bath. The shear force is achieved by means of a perforated disk immersed in the mixture, which is made to vibrate along a direction normal to its main surface (frequency 60 Hz, amplitude ca. 0.05–0.2 mm). A thick, homogeneous slurry is obtained. Upon reaching 12° C., 214 g of the slurry are filtered on a Buchner funnel. 47 g filtrate are obtained. The precipitate (167 g) is reslurried at 14° C. with 46 g saturated solution of pure nicotinamide and then refiltered. In this manner no crystals of nicotinamide will dissolve in the wash liquid. The nicotinic acid (ammonium nicotinate) dissolved in the mother liquor, which adheres to the crystals after the filtration, will be diluted by the wash liquid. Upon filtration, the amount of nicotinic acid dissolved in the mother liquor adhering to the crystals will be less than before. The reslurrying and filtration are repeated two more times under essentially the same conditions. After the initial filtration and after the second and third washings, samples of the precipitate are collected and analyzed for nicotinic acid. The results, expressed as wt% nicotinic acid in the dry precipitate, are compared in the table below to those calculated (by using the actual weights of the precipitate, filtrate and wash liquid) by assuming that the whole amount of nicotinic acid is dissolved in the mother liquor adhering to the crystals.

|  | Wt % Nicotinic Acid (dry basis) | |
| --- | --- | --- |
|  | Calculated | Actual |
| Initial mixture | — | 7.03 |
| Precipitate after filtration | 4.15 | 4.74 |
| Precipitate after 1st wash | 2.70 | — |
| Precipitate after 2nd wash | 1.41 | 0.80;0.81 |
| Precipitate after 3rd wash | 0.74 | 0.51;0.42 |

The above results show that by proceeding in accordance with the invention the nicotinic acid present as ammonium nicotinate in the initial slurry neither forms mixed crystals with the nicotinamide nor is occluded in its crystals; accordingly, a high degree of purification is achieved.

Numerous modifications and variations of the present invention are possible in light of the above teachings, and therefore, within the scope of the appended claims, the invention may be practised otherwise than as particularly described.

I claim:

1. A process for recovering nicotinamide from an aqueous solution of nicotinamide, which solution when subjected to rapid cooling produces a non-filterable solid, comprising:
   rapidly cooling said solution to crystallize nicotinamide from the solution, and applying to the nicotinamide and water a high shear force field sufficient to produce a filterable slurry of the nicotinamide.

2. The process of claim 1 wherein said shear force field is applied subsequent to said rapid cooling to a solid-like aggregate of nicotinamide and water.

3. The process of claim 1 wherein the shear force field is applied during said rapid cooling.

4. The process of claim 1 wherein the nicotinamide concentration is at least 40%.

5. The process of claim 4 wherein the shear force field is applied during the cooling.

6. The process of claim 5 wherein the shear force field is applied subsequent to the cooling to a solid-like aggregate of the nicotinamide and water.

* * * * *